United States Patent
Wolf et al.

(10) Patent No.: US 7,686,838 B2
(45) Date of Patent: Mar. 30, 2010

(54) EXTERNAL BULLET ANCHOR APPARATUS AND METHOD FOR USE IN SURGICAL REPAIR OF LIGAMENT OR TENDON

(75) Inventors: Alan W. Wolf, Ketchikan, AK (US); Christopher S. Jordan, Midwest City, OK (US)

(73) Assignee: ArthroCare Corporation, Austin, TX (US)

( * ) Notice: Subject to any disclaimer, the term of this patent is extended or adjusted under 35 U.S.C. 154(b) by 563 days.

(21) Appl. No.: 11/595,353

(22) Filed: Nov. 9, 2006

(65) Prior Publication Data

US 2008/0275553 A1    Nov. 6, 2008

(51) Int. Cl.
    *A61B 17/86*    (2006.01)
    *A61B 17/04*    (2006.01)
    *A61B 17/84*    (2006.01)
    *A61F 2/08*    (2006.01)

(52) U.S. Cl. ............... 606/325; 606/300; 623/13.14
(58) Field of Classification Search ............... 623/13.11, 623/13.14, 13.15; 606/232, 300, 325, 328
See application file for complete search history.

(56) References Cited

U.S. PATENT DOCUMENTS

| | | | |
|---|---|---|---|
| 3,896,500 A | 7/1975 | Rambert et al. | 623/13.14 |
| 3,973,277 A | 8/1976 | Semple et al. | 623/13.14 |
| 4,126,165 A | 11/1978 | Guignard et al. | 142/56 |
| 4,149,277 A | 4/1979 | Bokros | 623/13.2 |
| 4,187,558 A | 2/1980 | Dahlen et al. | 623/13.14 |
| 4,204,544 A | 5/1980 | Feldstein et al. | 600/375 |
| 4,275,717 A | 6/1981 | Bolesky | 606/63 |

(Continued)

FOREIGN PATENT DOCUMENTS

DE    9002844    1/1991

(Continued)

OTHER PUBLICATIONS

Carleton Sports Medicine, *Graft Choices in ACL Reconstruction* www.carletonsportsmed.com/graftacl.htm.

(Continued)

*Primary Examiner*—David Isabella
*Assistant Examiner*—Joshua Levine
(74) *Attorney, Agent, or Firm*—Matthew Scheele; Brian E. Szymczak

(57) ABSTRACT

A surgical anchor device for the repair of a torn ligament or tendon, primarily the anterior cruciate ligament in the knee, is used to affix the ligament within a femoral bone tunnel in the distal portion of the femur from the intra-articular surface, the device providing a pulley for a suture, wherein a free end of the suture may be pulled away from the device to draw the suture attached to the ligament graft within the femoral bone tunnel securing the ligament graft within the bone tunnel. Installation of the device is provided by insertion of the device through a tibial hole, through the femoral tunnel out of the lateral femoral cortex, pulling the attached sutures simultaneously to flatten the device against the lateral femoral cortex, attaching one end of the suture to the ligament graft and pulling the other end of the suture until the graft is situated properly within the femoral bone tunnel and tying the free end of the suture to retain the graft within the femoral bone tunnel.

1 Claim, 3 Drawing Sheets

U.S. PATENT DOCUMENTS

| | | | |
|---|---|---|---|
| 4,309,778 A | 1/1982 | Buechel et al. | 623/20.29 |
| 4,708,132 A | 11/1987 | Silvestrini | 606/66 |
| 4,712,542 A | 12/1987 | Daniel et al. | 606/96 |
| 4,776,851 A | 10/1988 | Bruchman et al. | 623/13.11 |
| 4,950,270 A | 8/1990 | Bowman et al. | 606/72 |
| 4,997,433 A | 3/1991 | Goble et al. | 606/64 |
| 5,037,422 A | 8/1991 | Hayhurst et al. | 606/72 |
| 5,037,426 A | 8/1991 | Goble et al. | 606/96 |
| 5,046,513 A | 9/1991 | Gatturna et al. | 128/898 |
| 5,112,338 A | 5/1992 | Anspach, III | 606/99 |
| 5,139,520 A | 8/1992 | Rosenberg | 606/87 |
| 5,147,361 A | 9/1992 | Ojima et al. | 606/61 |
| D330,591 S | 10/1992 | Rosenberg et al. | D24/147 |
| 5,152,790 A | 10/1992 | Rosenberg et al. | 623/13.14 |
| 5,176,682 A | 1/1993 | Chow | 606/72 |
| 5,258,003 A | 11/1993 | Ciaglia et al. | 606/185 |
| 5,258,016 A | 11/1993 | Dipoto et al. | 606/232 |
| 5,266,075 A | 11/1993 | Clark et al. | 606/138 |
| 5,306,301 A | 4/1994 | Graf et al. | 623/13 |
| 5,324,308 A | 6/1994 | Pierce | 606/232 |
| 5,330,468 A | 7/1994 | Burkhart | 606/96 |
| 5,350,380 A | 9/1994 | Goble et al. | 606/80 |
| 5,350,383 A | 9/1994 | Schmieding et al. | 606/96 |
| 5,364,400 A | 11/1994 | Rego, Jr. et al. | 606/72 |
| RE34,871 E | 3/1995 | McGuire et al. | 606/73 |
| 5,405,359 A | 4/1995 | Pierce | 606/232 |
| 5,423,860 A | 6/1995 | Lizardi et al. | 606/232 |
| 5,472,452 A | 12/1995 | Trott | 606/232 |
| 5,556,411 A | 9/1996 | Taoda et al. | 606/185 |
| 5,591,190 A | 1/1997 | Yoon | 606/185 |
| 5,591,232 A * | 1/1997 | Rahimi et al. | 128/898 |
| 5,601,562 A | 2/1997 | Wolf et al. | 606/86 |
| 5,609,634 A | 3/1997 | Voydeville | 623/13.11 |
| 5,618,314 A | 4/1997 | Harwin et al. | 606/232 |
| 5,632,748 A | 5/1997 | Beck et al. | 606/89 |
| 5,643,266 A | 7/1997 | Li | 606/72 |
| 5,645,588 A | 7/1997 | Graf | |
| 5,647,874 A | 7/1997 | Hayhurst | 606/72 |
| 5,674,224 A | 10/1997 | Howell et al. | 606/88 |
| 5,683,471 A | 11/1997 | Incavo et al. | 128/898 |
| 5,707,395 A | 1/1998 | Li | 606/232 |
| 5,713,897 A | 2/1998 | Goble et al. | 606/53 |
| 5,725,541 A | 3/1998 | Anspach et al. | 606/151 |
| 5,733,307 A | 3/1998 | Dinsdale | 606/232 |
| 5,735,867 A | 4/1998 | Golser et al. | 606/185 |
| 5,769,894 A | 6/1998 | Ferragamo | |
| 5,782,749 A | 7/1998 | Riza | 600/117 |
| 5,791,350 A | 8/1998 | Morton | 600/590 |
| 5,797,963 A | 8/1998 | McDevitt | 606/232 |
| 5,813,808 A | 9/1998 | Wu | 411/32 |
| 5,814,070 A | 9/1998 | Borzone et al. | 606/232 |
| 5,840,078 A | 11/1998 | Yerys | 606/151 |
| 5,871,504 A | 2/1999 | Eaton et al. | 606/232 |
| 5,891,150 A | 4/1999 | Chan | 606/96 |
| 5,891,168 A | 4/1999 | Thai | 606/72 |
| 5,895,425 A | 4/1999 | Grafton et al. | 606/73 |
| 5,913,860 A | 6/1999 | Scholl | 606/100 |
| 5,918,604 A | 7/1999 | Whelan | 128/898 |
| 5,935,129 A | 8/1999 | McDevitt et al. | 606/72 |
| 5,984,966 A | 11/1999 | Kiema et al. | 623/13.14 |
| 5,989,253 A | 11/1999 | Bigliardi | 606/72 |
| 6,056,752 A | 5/2000 | Roger | |
| 6,068,648 A | 5/2000 | Cole et al. | 606/232 |
| D426,305 S | 6/2000 | Hein | D24/147 |
| 6,080,154 A | 6/2000 | Reay-Young et al. | 606/60 |
| 6,086,591 A | 7/2000 | Bojarski | |
| 6,099,568 A | 8/2000 | Simonian | |
| 6,110,207 A | 8/2000 | Eichhorn et al. | 623/13.14 |
| 6,117,161 A | 9/2000 | Li et al. | 606/232 |
| 6,132,433 A | 10/2000 | Whelan | 606/72 |
| 6,146,406 A | 11/2000 | Shluzas et al. | 606/232 |
| 6,146,407 A | 11/2000 | Krebs | 606/232 |
| 6,152,928 A | 11/2000 | Wenstrom | 606/72 |
| 6,156,039 A | 12/2000 | Thai | 606/72 |
| 6,187,011 B1 | 2/2001 | Torrie | 606/96 |
| 6,214,007 B1 | 4/2001 | Anderson | 606/73 |
| 6,221,107 B1 | 4/2001 | Steiner et al. | 623/13.14 |
| 6,224,603 B1 | 5/2001 | Marino | 606/79 |
| 6,306,138 B1 | 10/2001 | Clark et al. | 606/65 |
| 6,319,270 B1 | 11/2001 | Grafton et al. | 606/232 |
| 6,328,758 B1 | 12/2001 | Tornier et al. | 606/232 |
| 6,355,053 B1 | 3/2002 | Li | 606/232 |
| 6,355,066 B1 | 3/2002 | Kim | 623/13.14 |
| 6,371,124 B1 | 4/2002 | Whelan | 128/898 |
| 6,379,361 B1 | 4/2002 | Beck, Jr. et al. | 606/72 |
| 6,402,757 B1 | 6/2002 | Moore, III et al. | 606/80 |
| 6,440,134 B1 | 8/2002 | Zaccherotti | |
| 6,491,714 B1 | 12/2002 | Bennett | 606/232 |
| 6,499,486 B1 | 12/2002 | Chervitz et al. | 128/898 |
| 6,517,542 B1 | 2/2003 | Papay et al. | 606/232 |
| 6,517,578 B2 | 2/2003 | Hein | 623/13.13 |
| 6,527,795 B1 | 3/2003 | Lizardi | 606/232 |
| 6,533,802 B2 | 3/2003 | Bojarski | |
| 6,533,816 B2 | 3/2003 | Sklar | 623/13.14 |
| 6,544,273 B1 | 4/2003 | Harari et al. | 606/151 |
| 6,547,800 B2 | 4/2003 | Foerster et al. | 606/151 |
| 6,551,343 B1 | 4/2003 | Tormala et al. | 606/213 |
| 6,554,553 B2 | 4/2003 | Freedland | 411/392 |
| 6,562,071 B2 | 5/2003 | Jarvinen | 623/13.14 |
| 6,599,289 B1 | 7/2003 | Bojarski et al. | 606/60 |
| 6,610,064 B1 | 8/2003 | Goble et al. | 606/72 |
| 6,610,080 B2 | 8/2003 | Morgan | 606/232 |
| 6,623,524 B2 | 9/2003 | Schmieding | 623/13.14 |
| 6,635,074 B2 | 10/2003 | Bartlett | 606/232 |
| 6,652,560 B1 | 11/2003 | Gerke et al. | 606/232 |
| 6,685,728 B2 | 2/2004 | Sinnott et al. | 606/232 |
| 7,175,632 B2 | 3/2004 | Singhatat et al. | 606/72 |
| 6,736,847 B2 | 5/2004 | Seyr et al. | 623/13.14 |
| 6,780,188 B2 | 8/2004 | Clark et al. | 606/73 |
| 6,802,862 B1 | 10/2004 | Roger et al. | 623/13.14 |
| 6,808,528 B2 | 10/2004 | Justin | 606/72 |
| 6,878,166 B2 | 4/2005 | Clark et al. | 623/13.12 |
| 6,905,513 B1 | 6/2005 | Metzger | 623/20.17 |
| 6,994,725 B1 | 2/2006 | Goble | 623/13.14 |
| 7,001,429 B2 | 2/2006 | Ferguson | |
| 7,063,717 B2 | 6/2006 | Pierre et al. | 606/232 |
| 7,083,647 B1 | 8/2006 | Sklar et al. | 623/13.14 |
| 7,226,469 B2 | 6/2007 | Benavitz et al. | 606/232 |
| D547,451 S | 7/2007 | Asfora | D24/146 |
| 7,285,121 B2 | 10/2007 | Braun et al. | 606/279 |
| 7,338,492 B2 * | 3/2008 | Singhatat et al. | 606/232 |
| 2002/0038231 A1 | 3/2002 | Visotsky et al. | 606/73 |
| 2004/0193167 A1 | 9/2004 | Tucciarone et al. | 606/73 |
| 2005/0075636 A1 * | 4/2005 | Gotzen | 606/72 |
| 2005/0222619 A1 | 10/2005 | Dreyfuss et al. | 606/72 |
| 2006/0235516 A1 | 10/2006 | Cavazzoni | 623/13.14 |
| 2006/0253119 A1 | 11/2006 | Berberich et al. | 606/72 |
| 2006/0276841 A1 | 12/2006 | Barbieri et al. | 606/232 |
| 2007/0021751 A1 | 1/2007 | Reay-Young et al. | 606/72 |
| 2007/0213730 A1 | 9/2007 | Martinek et al. | 606/72 |
| 2007/0260249 A1 | 11/2007 | Boyajian et al. | 606/72 |
| 2008/0288069 A1 | 11/2008 | Wolf et al. | 606/301 |

FOREIGN PATENT DOCUMENTS

| | | |
|---|---|---|
| DE | 29607352 | 9/1996 |
| EP | 238223 | 9/1987 |
| EP | 279129 | 8/1988 |
| EP | 317406 | 5/1989 |
| EP | 379789 | 11/1989 |
| EP | 346469 | 12/1989 |
| EP | 574707 | 12/1993 |
| EP | 619982 | 3/1994 |
| EP | 0 674 880 | 3/1995 |

| | | |
|---|---|---|
| EP | 0865774 | 9/1998 |
| EP | 1066805 | 6/2000 |
| EP | 1180351 | 2/2002 |
| FR | 2395012 | 1/1979 |
| FR | 2590792 | 6/1987 |
| FR | 2683715 | 5/1993 |
| FR | 2725615 | 4/1996 |
| FR | 2732211 | 4/1996 |
| GB | 2288739 | 11/1995 |
| GB | 2337463 | 11/1999 |
| SU | 1521465 | 11/1989 |
| WO | 93/25148 | 12/1993 |
| WO | 95/11631 | 5/1995 |
| WO | 96/29029 | 9/1996 |
| WO | 96/39934 | 12/1996 |
| WO | 97/20522 | 6/1997 |
| WO | 98/12991 | 4/1998 |
| WO | 98/12992 | 4/1998 |
| WO | 98/22048 | 5/1998 |
| WO | 98/38937 | 9/1998 |
| WO | 99/52472 | 10/1999 |
| WO | 99/59488 | 11/1999 |
| WO | 03/088874 | 10/2003 |

OTHER PUBLICATIONS

Ortheon Medical, Distal Tendon Repair with the Lubbers Technique, www.ortheon.com/distal.htm.
Smith & Nephew, "Arthroscopic Repair of a Bankart Lesion Using TAG Suture Anchors," 12 pgs, May 1996.
F.H. Fuh, et al., Anatomic ACL Double-Bundle Reconstruction, Orthopedic Technology Review vol. 7 No. 4, 6 pgs, 2005.
Daily Updates, "ACL Reconstruction Using a Double-Looped Semi-tendinous and Gracilis (DLSTG) Hamstring Graft with the Bone Much Screw and Sasherloc Device from Arthrotec", <www.ptupdate.com/members/daily/Art012602.htm> Printed Aug. 21, 2006.
UK Search Report for GB 9915550, 1 pg, Jun. 13, 2000.
UK Search Report for GB 0116605, 1 pg, Mar. 27, 2002.
UK Search Report for GB 0208667, 1 pg, Feb. 24, 2003.
European Search Report for EP 00113471, 2 pgs, Jan. 26, 2001.
European Search Report for EP 02014485, 2 pgs, Nov. 4, 2003.
European Search Report for EP 98301702, 2 pgs, Jun. 23, 1998.
PCT International Search Report for PCT/GB03/01606, 3 pgs, Mailed Sep. 4, 2003.
PCT Notification of the International Search Report and Written Opinion for PCT/US05/17382, 11 pgs, Mailed Oct. 23, 2007.

* cited by examiner

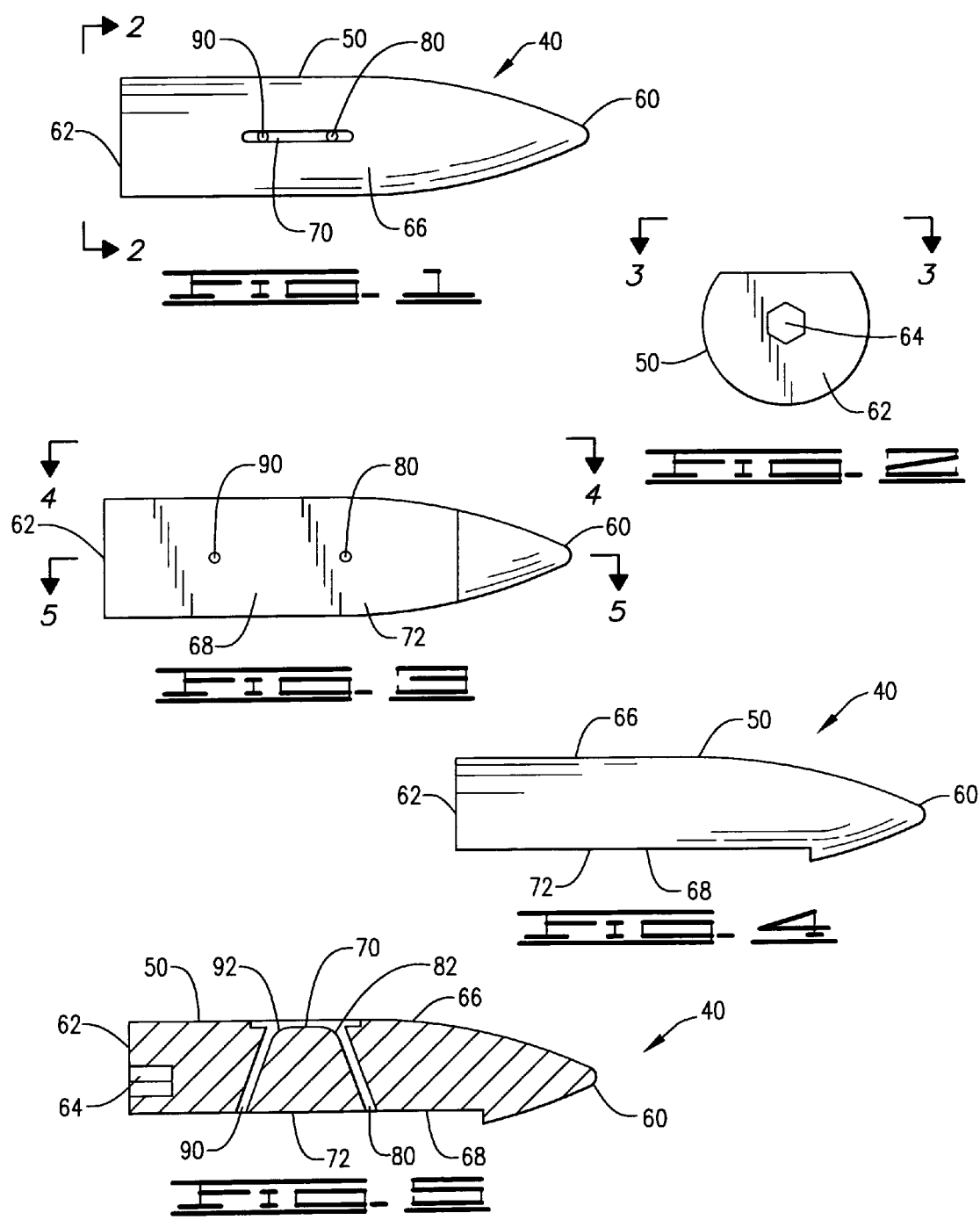

EXTERNAL BULLET ANCHOR APPARATUS AND METHOD FOR USE IN SURGICAL REPAIR OF LIGAMENT OR TENDON

CROSS REFERENCE TO RELATED APPLICATIONS

None

I. BACKGROUND OF THE INVENTION

1. Field of Invention

A surgical anchor device for the repair of a torn ligament or tendon, primarily the anterior cruciate ligament in the knee, is used to affix the ligament within a femoral bone tunnel in the distal portion of the femur from the intra-articular surface, the device providing a pulley for a suture, wherein a free end of the suture may be pulled away from the device to draw the suture attached to the ligament graft within the femoral bone tunnel securing the ligament graft within the bone tunnel. Installation of the device is provided by insertion of the device through a tibial hole, through the femoral tunnel out of the lateral femoral cortex, pulling the attached sutures simultaneously to flatten the device against the lateral femoral cortex, attaching one end of the suture to the ligament graft and pulling the other end of the suture until the graft is situated properly within the femoral bone tunnel and tying the free end of the suture to retain the graft within the femoral bone tunnel.

2. Description of Prior Art

The following United States patents were discovered and are disclosed within this application for utility patent. All relate to orthopedic surgical anchor devices.

A first category of prior art includes devices known and referenced as endo-buttons. These are devices which are attached to sutures to retain a portion of the suture on the outside of a hole in the bone to prevent withdrawal of the suture back into the hole in the bone. Such devices may be found in advertisements by TENOFIX® and ACUFEX®. Endo-button style devices may also be found in U.S. Pat. Nos. 5,769,894 to Ferragamo and 6,099,568 to Simonian.

A device for the femoral fixation of tendons in ACL repair is disclosed in U.S. Pat. No. 6,440,134 to Zaccherotti. This device provides an elongated body having a first end defining a passage for retaining the tendons to the body, a set bar pivotally supported within the second end about a transverse axis with the set bar having two extending stop arms. The tendon is attached through the passage and the body is inserted through the tunnels in the tibia and femur second end first with the set bar in the same direction as the body of the device until the second end extends through the outer surface of the femur. The set bar is then rotated perpendicular to the body with the set arms extended, retaining the body and connected tendon within the femoral tunnel with a fixed tension upon the tendon and ligament.

In U.S. Pat. No. 6,086,591 to Bojarski, a soft tissue anchor is disclosed having a body, a first end defining a passage for attaching soft tissue to the anchor and a second end defining a hook having a sharp rounded tip, the anchor being inserted into a first tunnel through the tibia extending into the femur to a reduced diameter tunnel in the femur which is the same length as the body and second end of the anchor. The soft tissue attaches to the first end of the anchor and is pushed through the tunnel until the hook is extended through the outer surface of the femur, the hook engaging the outer surface of the femur to retain the anchor and tendon within the bone tunnel.

II. SUMMARY OF THE INVENTION

In the event an ACL incurs a complete tearing from the posterior femoral cortex, surgical repair requires the attachment of the torn ligament within the distal portion of the femur. Common techniques of the past indicate the drilling of a tunnel from the upper anterior surface of the tibia into the distal portion of the femur while the knee is bent at a right angle. This is seen in the disclosed prior art. However, the prior art discloses a fixation of the ligament or tendon to a surgical device prior to insertion of the anchor into the tunnel. The ligament or tendon is stretched during insertion of the anchors within the tunnels with the tendon or ligament being set at the time of complete insertion of the anchor.

The present device is a bullet-shaped anchor which is inserted through a bone tunnel drilled through the upper anterior portion of the tibia and through the distal end of the femur while the knee in bent at a ninety degree angle, completely through the lateral cortex of the distal femur without penetration of the skin overlying the femur. The device is flattened on a side portion and bluntly shaped at a first end. The flattened side portion contains a lower and upper laterally tapering aperture joining at a transitional groove in the opposing side of the device, wherein a suture may be passed through the upper laterally tapering aperture, within the transitional groove and out the lower laterally tapering aperture, with the ends of the suture extending from the device. The device is inserted through the bone tunnel out the lateral femoral cortex using an elongated tool adapted to be inserted in an indented socket in the base of the device opposite the first end. It is then disengaged from the tool. The two ends of the suture are then simultaneously pulled to place the flattened side of the device against the lateral femoral bone surface, the two ends of the sutures being pulled back and forth, the device acting as a pulley. One end of the suture is attached to the ACL graft, while the other may be pulled to elevated the ACL graft into the bone tunnel in the femur.

The primary objective of the invention is to provide a fixed anchor acting as a pulley for a suture to secure a tendon or ligament graft between the tibia and the femur. A second objective is to provide the device to be inserted without requiring a puncture wound to the lateral femoral skin which can result in contamination or running a risk of interfering with the placement of the tourniquet or thigh holder used during the ACL surgery.

III. DESCRIPTION OF THE DRAWINGS

The following drawings are submitted with this utility patent application.

FIG. 1 is a top view of the bullet anchor device.

FIG. 4 is a side view of the device along section lines 4/4 of FIG. 3.

FIG. 5 is a cross-sectional view of the device along section lines 5/5 of FIG. 3.

FIG. 6 is a view of the device being inserted through a bone tunnel in the upper anterior portion of the tibia into the lower posterior portion of the femur using a tool with the sutures attached to the device.

FIG. 7 is a view of the device installed against the lower anterior portion of femur with one end of the suture attached to the ligament or tendon graft with the free end of the suture extending through the bone tunnel to draw the ligament or tendon graft into the bone tunnel in the femur.

IV. DESCRIPTION OF THE PREFERRED EMBODIMENT

Figure 3:
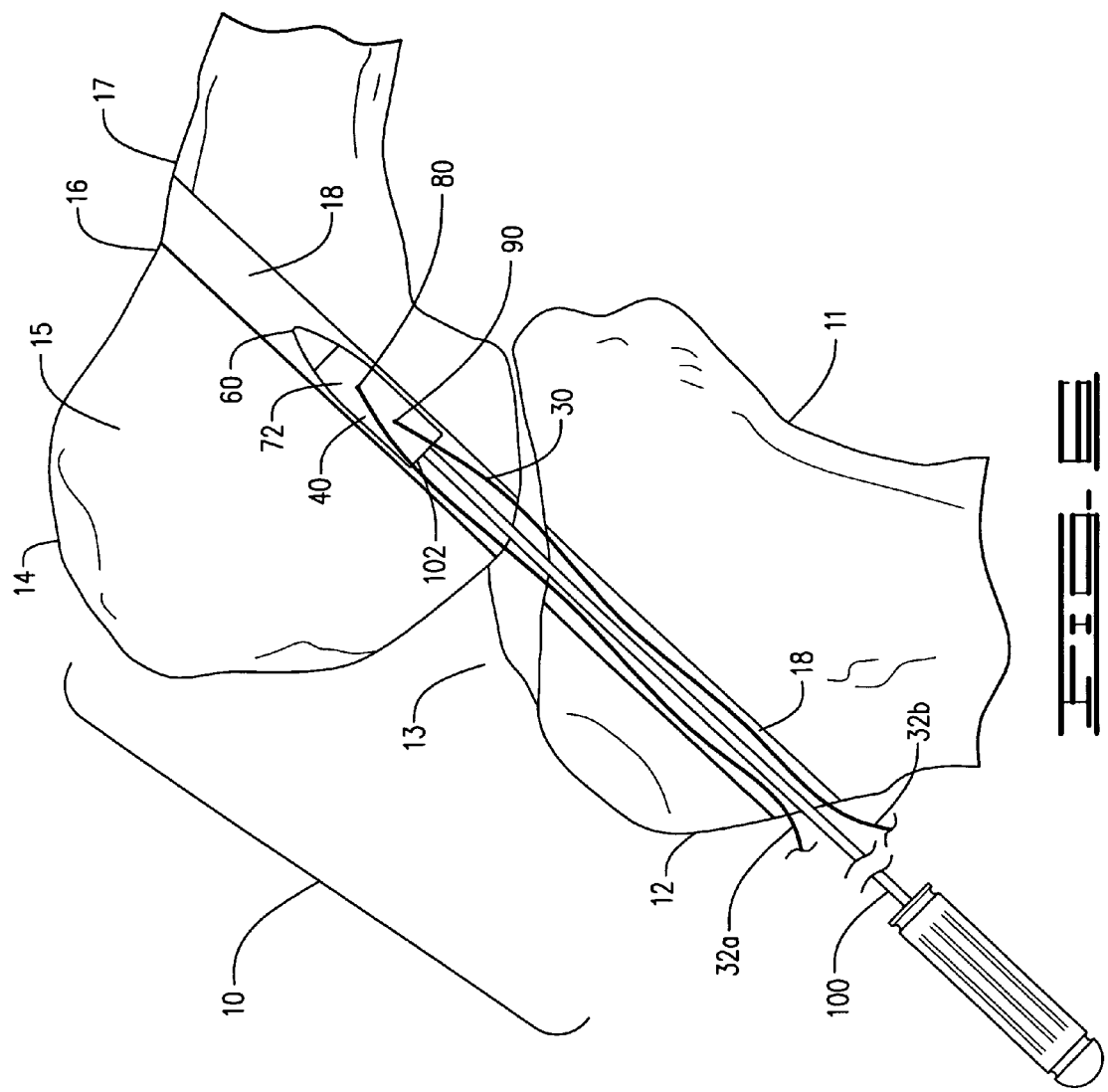
FIG. 3 is a bottom view of the device along section lines 3/3 of FIG. 2.
Figure 2:
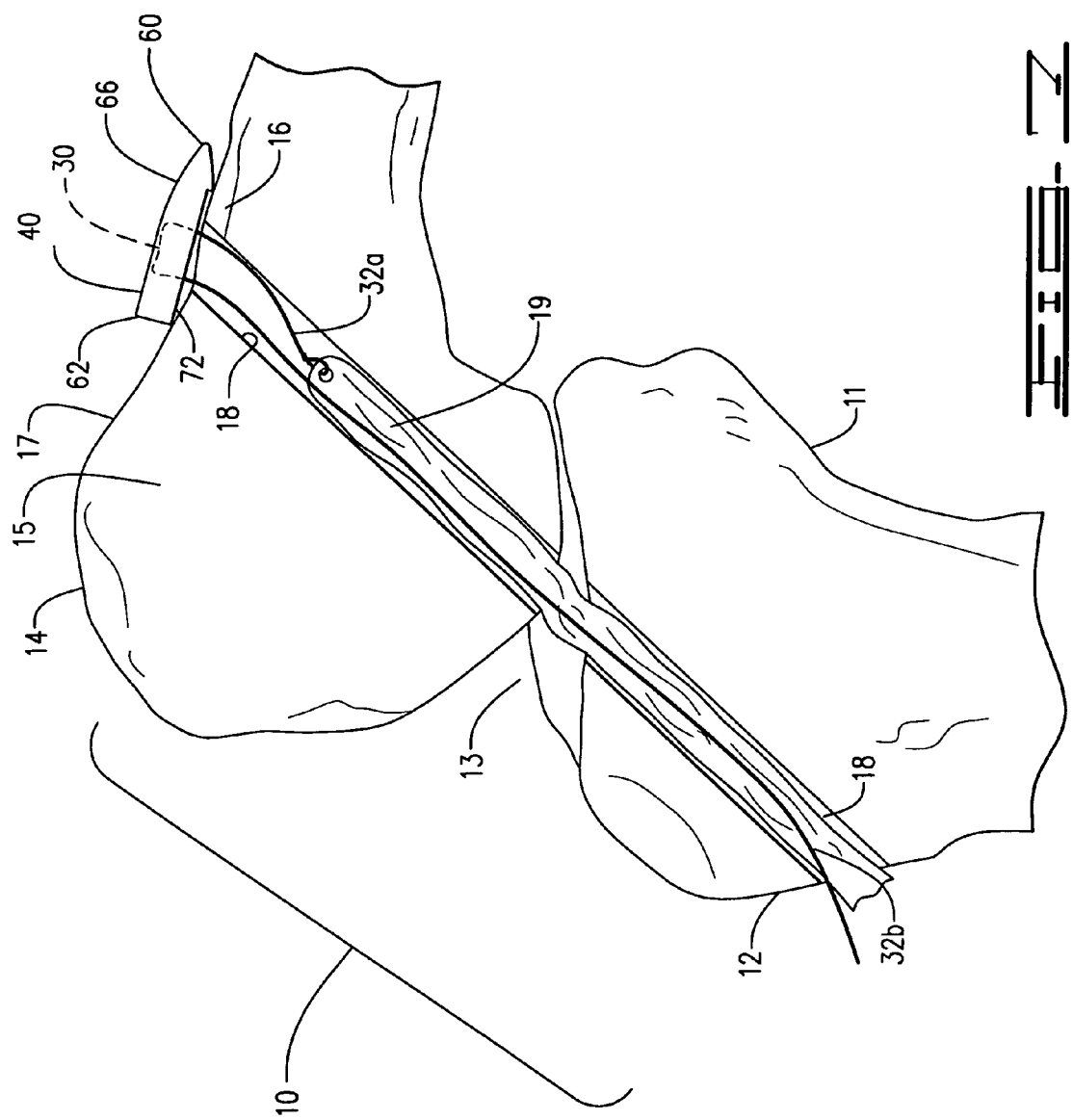
FIG. 2 is a lower end view of the device along section lines 2/2 of FIG. 1.

A bullet anchor device 40 is utilized in the surgical repair and attachment of a tendon or ligament graft in a joint, specifically the attachment of an ACL graft 19 within a knee 10, the device 40 comprising a body member 50 having a blunt tapered first end 60, FIGS. 1 and 3-5, a flat second end 62 defining an indented tool socket 64, FIG. 2, an upper surface 66 providing an axial recessed groove 70, FIG. 1, a lower surface 68 defining a flattened portion 72, FIGS. 3 and 4, an upper aperture 80 from the flattened portion 72 to the recessed groove 70, and a lower aperture 90 from the flattened portion 72 to the recessed groove 70, FIGS. 1, 3 and 5, the upper and lower apertures 80, 90, and the recessed groove 70 adapted to receive a surgical suture 30 having two ends 32*a*, 32*b*, extending from the upper and lower apertures 80, 90, FIGS. 6 and 7. The device is preferably made from a biocompatible material.

Most preferably, as indicated in FIG. 5, the upper and lower apertures 80, 90, are angled, having an inward taper from the flattened portion 72 to the recessed groove 70, with a smooth rounded lower margin 92 and a smooth rounded upper margin 82 adjacent to the upper and lower apertures 80, 90, preventing any sharp edge from being in contact with the suture 30 passing through the upper and lower apertures 80, 90 and the recessed margins 82, 92. The suture should pass freely through the upper and lower apertures 80, 90, and within the recessed groove 70, as the device is provided as a pulley for the suture 30 to be drawn back and forth through the device.

Although having the potential for reattachment of any ligament in a joint, the device 40 as utilized in an ACL surgical repair would require surgical preparation of the knee 10, including the placement of the knee 10 at a ninety degree angle with the leg retained in a thigh-holder. A tourniquet is applied above the knee 10. After the skin is properly cleaned and sterilized, an incision is made in the skin covering the upper anterior portion 12 of the tibia 11, and a bone tunnel 18 is drilled from the upper anterior portion 12 of the tibia 11 through the knee capsule 13 and completely through the distal end 15 of the femur 14 to the lateral femoral cortex 16, but without penetration of the skin covering the lateral femoral cortex 16, FIGS. 6 and 7. After debridement of the bone tunnel 18, having a suture 30 pre-threaded with the device 40, the tapered first end 60 of the device 40 is inserted into the bone tunnel 18 from tibia 11 through femur 14 using an elongated tool 100 having an end 102 adapted to the indented tool socket 64 to rotate and insert the device 10 through the bone tunnel 18 to the lateral femoral cortex 16, FIG. 7. The two ends 32*a*, 32*b* of the suture 30 are then simultaneously pulled to secure the lower surface 68 against the outer surface 17 of the lateral femoral cortex 16. One end 32*a* of the suture 30 is attached and secured to the ACL graft 19, after which the unattached end 32*b* of the suture 30 is pulled from the bone tunnel 18 drawing the ACL graft 19 into the bone tunnel 18 of the femur 14, the device 10 acting as a pulley upon the suture 30, FIG. 7. After the ACL graft 19 is drawn to an optimal tension and length within the bone tunnel 18 in the femur 14, the unattached end 32*b* of the suture 30 is tied off, either to the ACL graft 19 or to another suitable structure to maintain tension on the ACL graft 19. Any excess length of the suture 30 is trimmed off and the external wound or incision is closed.

While the invention has been particularly shown and described with reference to a preferred embodiment thereof, it will be understood by those skilled in the art that changes in form and detail may be made therein without departing from the spirit and scope of the invention.

What is claimed is:

1. A method for the surgical repair of an anterior cruciate ligament in a knee comprising the steps of:
    positioning said knee joint at a ninety degree angle;
    preparing said knee for surgery by sterilization of said knee;
    drilling a bone tunnel from an upper anterior portion of a tibia through a knee capsule and completely through a distal end of a femur to a lateral femoral cortex;
    inserting a blunt tapered first end of a biocompatible bullet anchor device into said bone canal of said upper anterior portion of said tibia, said bullet anchor device further comprising a flat second end defining an indented tool socket, an upper surface providing an axial recessed groove, a lower surface defining a flattened portion, an upper aperture from said flattened portion to said recessed groove, and a lower aperture from said flattened portion to said recessed groove, said upper and lower apertures and said recessed groove slideably securing a surgical suture having two ends extending from said bullet anchor device, said insertion accomplished by use of an elongated tool having an end adapted to said indented tool socket to rotate and insert said bullet anchor device completely through said bone tunnel to said lateral femoral cortex;
    simultaneously pulling said two ends of said suture until said lower surface is secured against an outer surface of said lateral femoral cortex;
    securing a first of said two ends of said suture to an ACL graft;
    pulling a second of said two ends of said suture from said bone tunnel while drawing said ACL graft into said bone tunnel, said device acting as a pulley upon said suture;
    tying off the second of said two ends of said suture to said ACL graft or other suitable structure within said knee joint.

* * * * *